United States Patent
Xiong et al.

(10) Patent No.: US 12,233,050 B2
(45) Date of Patent: Feb. 25, 2025

(54) DRUG AND GENE THERAPY TO TREAT HIGH MYOPIA AND OTHER OCULAR DISORDERS WITH ENLARGED EYE GLOBES

(71) Applicant: City University of Hong Kong, Kowloon (HK)

(72) Inventors: Wenjun Xiong, Kowloon (HK); Shuyi Mai, Kowloon (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 634 days.

(21) Appl. No.: 17/346,036

(22) Filed: Jun. 11, 2021

(65) Prior Publication Data

US 2021/0386714 A1 Dec. 16, 2021

Related U.S. Application Data (60) Provisional application No. 63/038,163, filed on Jun. 12, 2020.

(51) Int. Cl.

| | | |
|---|---|---|
| C12N 15/86 | (2006.01) | |
| A61K 31/21 | (2006.01) | |
| A61K 31/426 | (2006.01) | |
| A61K 48/00 | (2006.01) | |
| C07H 21/04 | (2006.01) | |
| C12N 15/864 | (2006.01) | |

(52) U.S. Cl.
CPC ............ *A61K 31/426* (2013.01); *A61K 31/21* (2013.01); *A61K 48/0058* (2013.01); *C12N 15/86* (2013.01); *C07H 21/04* (2013.01); *C12N 15/8645* (2013.01); *C12N 2750/14143* (2013.01)

(58) Field of Classification Search
CPC .. A61K 48/005; A61K 48/0058; C12N 15/79; C12N 15/86; C12N 15/8645; C12N 2750/14143; C07H 21/04
See application file for complete search history.

(56) References Cited

PUBLICATIONS

Center of Disease Control (CDC), 2024 (Vision Health Initiative (VHI), p. 1-8).*
National Institute of Health, 2024 (National Eye Institute, Eye Conditions and Diseases, p. 1-4).*
Longoni et al., 2018 (National Institute of Health, NCBI Bookself, p. 1-19).*
Kotterman et al., 2014 (Nature Reviews, vol. 15, p. 445-451).*
Shim et al., 2017 (Current Gene Therapy, vol. 17, No. 5, p. 1-18).*
Lenzi et al., 2014 (NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16).*
Bulcha et al., 2021 (Signal Transduction and Targeted Therapy, 6:53, p. 1-24).*
Drag et al., 2023 (IOVS, vol. 64, No. 7, article 39, p. 1-17).*
Namdev et al., 2016 (Research J. Pharm. and Tech., 9(3), p. 305-312).*
Rehman et al., 2016 (Current Drug targets, vol. 17, p. 1172-1188).*
Mun et al., 2022 (Journal of Controlled Release, vol. 350, p. 716-733).*

* cited by examiner

*Primary Examiner* — Shin Lin Chen
(74) *Attorney, Agent, or Firm* — Conley Rose, P.C.; Michael W. Piper; Gayatry Nair (57) ABSTRACT

A treatment of various eye conditions relating to eye enlargement is disclosed. The conditions can be treated with by inhibiting an upstream protein within the biological pathway or by increasing the expression of a downstream receptor within the same pathway. Inhibition of the upstream protein, sterol regulatory element binding protein (SREBP), has been achieved using small molecule inhibitors or nucleic acid in viral vector and increased expression of the downstream protein, bone morphogenetic protein (BMP), has been achieved by nucleic acid in viral vector. Also disclosed are the small molecule, nucleic acid and the viral vector as well as methods of treating ocular diseases.

3 Claims, 13 Drawing Sheets

Specification includes a Sequence Listing.

DRUG AND GENE THERAPY TO TREAT HIGH MYOPIA AND OTHER OCULAR DISORDERS WITH ENLARGED EYE GLOBES

This invention relates to a method and compositions for treatment of various eye conditions relating to eye enlargement. The conditions can be treated by inhibiting an upstream protein within a biological pathway or by increasing the expression of a downstream protein within the same pathway. Inhibition of the upstream protein, sterol regulatory element binding protein (SREBP), has been achieved using small molecule inhibitors or nucleic acid in viral vector and increased expression of the downstream receptor, bone morphogenetic protein (BMP), has been achieved by nucleic acid in viral vector. The invention relates to the small molecule, nucleic acid and the viral vector as well as methods of treating the ocular diseases.

BACKGROUND

Myopia, or near-sightedness, a leading cause of visual impairment, is reaching epidemic proportions in Asia and will affect half the global population by 2050. Despite this, the mechanisms regulating postnatal growth of the eye remain poorly understood.

The human eye continues to grow and elongate after birth. Average axial length of newborn babies is 16.8 mm, reaching 23.6 mm by adulthood. The deviation from the average adult axial length is quite small, with a standard deviation value of only 0.7 mm. Postnatal eye growth is most rapid in the first two years, which then continues at a slower rate through puberty. The control of eye growth, especially axial length, is of key importance to normal visual function; uncontrolled eye-growth can result in various ocular pathologies including high myopia. Although some consider myopia a simple nuisance, its incidence is dramatically increasing. The disease already affects 80-90% of young adults in Asia, and will affect 50% of the global population by 2050. About one billion will have high myopia, which can lead to complications such as myopic degeneration and retinal detachment that cause irreversible vision impairment.

Despite this urgency, the understanding of the mechanisms of visually guided eye growth, especially in the context of myopia development, remains poor. The genetic determinants of GROW and STOP signals that control eye size independent of visual experience are relatively understudied. The exact contributions of the many layers of the eye, from the retina, retinal pigment epithelium (RPE), choroid to sclera, in controlling and coordinating the growth of the posterior segment of the eye remains unknown. The RPE, which is a monolayer of polarized epithelial cells, resides at a key location between the choroid/sclera and the retina. Besides its function in maintaining retinal homeostasis, the RPE is also a major source of growth factors and cytokines, via which it can signal to and regulate the neighbouring tissues. Thus, the RPE could play a role in ocular growth regulation.

BRIEF SUMMARY OF THE DISCLOSURE

In a first aspect, the present invention provides a method of treating, preventing, reversing or delaying onset or progression of an ocular disorder in a subject in need thereof, comprising a step of administering to the subject a sterol regulatory element binding protein (SREBP) inhibitor.

Preferably the SREBP inhibitor can inhibit the activity or suppress the expression of a SREBP. Any potential method to inhibit SREBP can be used, whether that is gene silencing or small molecule inhibition or any other conceivable method. Gene silencing can be achieving by siRNA, shRNA, CRISPR or any other gene editing technique.

The invention also contemplates a sterol regulatory element binding protein (SREBP) inhibitor for use in a method of treating, preventing, reversing or delaying onset or progression of an ocular disorder.

In embodiments the ocular disorder is Donnai-Barrow syndrome, Facio-oculo-acoutstic-renal syndrome, Stickler syndrome, inherited high myopia, juvenile-onset myopia, buphthalmos, or vision loss preferably caused by eye enlargement; or the ocular disorder is associated with LRP gene deficiency, preferably LRP2 gene deficiency; or the ocular disorder is associated with BMP gene deficiency, preferably BMP2 or BMP4 gene deficiency.

The SREBP inhibitor may be administered to the subject via a topical route, suprachoroidal injection, subconjunctival route, intravitreal route, retrobulbar route, intracaemeral route, subretinal route, orally or intravenously, preferably via a subretinal or suprachoroidal injection route.

The step of administering to a subject or the route of administration may comprise contacting target cells of the subject with the SREBP inhibitor. Preferably said cells are Retinal Pigment Epithelium (RPE) cells.

The SREBP inhibitor may comprise or consist of a small molecule chemical, a protein, a nucleic acid sequence, or a nucleic acid in a vector.

The vector may be any vector known to the skilled person. For example, the vector may be a retrovirus, lentivirus, adenovirus, adeno-associated virus or a synthetic vector. Preferably, the vector is an adeno-associated virus.

The vector may further comprise a component capable of targeting or driving gene expression in RPE cells. For example, the vector may further comprise a promoter, which may be human Best1 gene promoter or RPE65 gene promoter.

In particular, the small molecule is administered orally or intravenously. The nucleic acid or the nucleic acid in a vector is preferably administered via a subretinal route or suprachoroidal route.

In certain embodiments the SREBP inhibitor is a SREBP inhibitor capable of inhibiting the expression of SREBP, the maturation of SREBP, the binding of SREBP to its cofactors, or the binding of SREBP to a target gene cis regulatory sequence.

In certain embodiments the SREBP inhibitor is a small molecule having at least two separated aromatic groups. The small molecule may optionally comprise a boronate group attached to one of the aromatic groups or a thiazine group separating the two aromatic groups. Preferably, the aromatic groups are independently phenyl or pyridyl.

In certain embodiments, the SREBP inhibitor is a small molecule having a structure of Formula (I) or Formula (II):

Formula (I)

Formula (II)

wherein
R¹ represents an alkenyl group (optionally a $C_{2-6}$ alkenyl group) substituted with a substituted or unsubstituted aryl ring (preferably a phenyl ring); when the aryl ring is substituted, it is substituted with 1 or 2 halo atoms;
R² represents a substituted or unsubstituted heteroaryl ring (preferably a pyridyl ring); when the heteroaryl ring is substituted, it is substituted with 1 or 2 alkyl groups (preferably $C_{1-6}$ alkyl groups); and
R³ represents an alkyl group (optionally a $C_{1-6}$ alkyl group).

R¹ may represent a $C_{2-6}$ alkenyl group substituted with an optionally substituted aryl ring (optionally a phenyl ring); when the aryl ring is substituted, it is substituted with 1 or 2 halo atoms.

R² may represent a substituted or unsubstituted pyridyl ring; when the pyridyl ring is substituted it is substituted with 1 or 2 alkyl groups (optionally $C_{1-6}$ alkyl groups).

R³ may represent a $C_{1-6}$ alkyl group.

Formulae (I) and (II) represent preferred embodiments of the present invention. However, the present invention also contemplates compounds having alternative points of substitution to those shown that are allowed by valency.

In certain embodiments the small molecule has a structure of Formula (III):

Formula (III)

wherein R⁴ represents an optionally substituted aryl ring (preferably a phenyl ring), when the aryl ring is substituted it is substituted with 1 or 2 halo atoms.

In certain embodiments the small molecule has a structure of Formula (IV):

Formula (IV)

wherein R⁵ represents an alkyl group (preferably $C_{1-6}$ alkyl group).

In certain embodiments the small molecule has a structure selected from:

The nucleic acid sequence or the nucleic acid in the vector may be a small interfering RNA (siRNA), a short hairpin RNA (shRNA) or CRIPSR all of which are for silencing SREBP.

The nucleic acid sequence may be: the sequence shown in SEQ ID NO:1, ID NO:2, or a homologue or a functional variant thereof.

The nucleic acid in a vector may be a vector comprising any of the nucleic acid sequences disclosed herein. For example, the vector may be AAV-hBest1-Srebp shRNA.

In a second aspect of the present invention, there is provided a method of treating, preventing, reversing or delaying onset or progression of an ocular disorder in a subject in need thereof, comprising a step of administering to the subject an agent that can increase the expression of bone morphogenetic protein 2 (BMP2) or bone morphogenetic protein 4 (BMP4).

The invention also contemplates an agent that can increase the expression of bone morphogenetic protein 2 (BMP2) or bone morphogenetic protein 4 (BMP4) for use in a method of treating, preventing, reversing or delaying onset or progression of an ocular disorder.

The ocular disorder may be selected from Donnai-Barrow syndrome, Facio-oculo-acoustic-renal syndrome, Stickler syndrome, inherited high myopia, juvenile-onset myopia, buphthalmos, or vision loss preferably related to eye enlargement; or the ocular disorder is associated with LRP gene deficiency, preferably LRP2 gene deficiency; or the ocular disorder is associated with BMP2 or BMP4 gene deficiency.

The agent may be administered to the subject via a topical route, suprachoroidal injection, subconjunctival route, intravitreal route, retrobulbar route, intracameral route, or subretinal route, preferably via a subretinal or suprachoroidal route.

The step of administering or the administration of the agent may comprise contacting target cells of the subject with the agent, preferably said cells are Retinal Pigment Epithelium (RPE) cells.

In certain embodiments, the agent comprises or consists of a small molecule chemical, a protein, a nucleic acid, or a nucleic acid in a vector.

The agent may comprise or consist of a nucleic acid sequence encoding BMP2 or a homologue thereof, a nucleic acid sequence encoding BMP4 or a homologue thereof, a BMP2, a BMP4, a BMP agonist protein that can activate BMP signalling pathway, or a combination thereof.

In a third aspect of the present invention there is provided a composition for treating an ocular disorder, or controlling axial growth of an eye of a subject, said composition comprising a) a SREBP inhibitor that can inhibit the activity or suppress the expression of a SREBP; b) an agent that can increase the expression of bone morphogenetic protein 2 (BMP2) or bone morphogenetic protein 4 (BMP4); and/or c) a vector comprising a Retinal Pigment Epithelium (RPE) cell-type specific promoter.

The vector may be an adeno-associated virus (AAV) vector and the vector comprises a nucleic acid sequence encoding BMP2 or a homologue thereof, or a nucleic acid sequence encoding BMP4 or a homologue thereof.

The SREBP inhibitor may be any small molecule or nucleic acid sequence disclosed herein. Preferably, the SREBP inhibitor has a structure of:

The SREBP inhibitor may have a nucleic acid sequence comprising the sequence shown in SEQ ID NO:1, ID NO:2, or a homologue or a functional variant thereof.

The agent comprises or consists of a nucleic acid sequence encoding BMP2 or a homologue thereof, a nucleic acid sequence encoding BMP4 or a homologue thereof, a BMP2, a BMP4, a BMP agonist protein that can activate BMP signalling pathway, or a combination thereof.

BRIEF DESCRIPTION OF THE DRAWINGS

Embodiments of the invention are further described by means of example but not in any limitative sense hereinafter with reference to the accompanying drawings, in which.

DETAILED DESCRIPTION

The term "small molecule" is a term recognized in the art. It is understood to be an organic molecule with a molecular weight of less than 900 Daltons. Thus, the small molecule of the present invention may be an organic molecule of less than 900 Daltons.

The present invention relates to the inhibition of Sterol Regulatory Element Binding Protein (Srebp2) which is a transcriptional repressor of the multi-ligand endocytic receptor Lrp2. The following examples show that Lrp2 deficiency or Srebp overexpression specifically in the retinal pigment epithelium (RPE) leads to high myopia in postnatal mice (FIG. 1). Overexpression of Srebp1a or Srebp2 in the RPE led to eye enlargement (FIG. 1), while suppression of endogenous Srebp2 prevented eye enlargement induced by Lrp2 knockdown (FIG. 2). It was further revealed that Bmp2 is downstream of Srebp-Lrp2. Excessive BMP2 causes microphthalmos, while insufficient BMP2 led to megalophthalmos (FIG. 1). RPE-specific overexpression of Bmp2 effectively rescued eye enlargement and retinal thinning caused by Lrp2 knockout (FIG. 3).

To separate the functions of Lrp2 in the RPE from other retinal cells, the phenotypes of RPE-specific Lrp2 knockdown were examined. Expression of GFP driven by a promoter of the RPE-specific gene Bestrophin-1 (Best1) could be observed as early as P1 and was largely restricted to the RPE. Restricting Lrp2 knockdown to the RPE was sufficient to reproduce the significant eye enlargement phenotype. To further exclude photoreceptor-derived Lrp2 from any role in initiating the eye enlargement phenotype, Lrp2 sh1 was specifically expressed in the photoreceptors with an AAV8 construct using a human rhodopsin kinase (RK) promoter that drives transgene expression specifically in rods and cones. The size of eyes between the AAV8-RK-Lrp2 sh1-injected and control groups were not noticeably different, suggesting that photoreceptor Lrp2 is not involved in restricting eye growth. These data suggest that RPE expression of Lrp2 normally functions to restrict neonatal eyes from excessive growth.

SREBP2 is a Transcriptional Repressor of Lrp2

SREBP2 acts as a transcriptional repressor of Lrp2, and Lrp2 is negatively regulated by Srebp2. nSrebp2 was selectively overexpressed in the RPE with an AAV driven by the Best1 promoter. Eyes injected with AAV8-Best1-nSrebp2 viruses had significantly increased globe size (FIG. 1). Suppressing Srebp2 expression rescued the eye enlargement phenotype induced by Lrp2 knockdown. Knockdown of Srebp2 by shRNA significantly rescued the phenotype caused by AAV8-Best1-Lrp2 sh1 (FIG. 2). A boron-containing small molecule BF175, shown below, was tested. In the mouse RPE explant model, adding BF175 to the culture medium reduced the mRNA level of Hmgcr and Ldlr, the two known SREBP2 transcriptional targets, while it significantly increased the mRNA level of Lrp2. The ability of BF175 to treat eye enlargement induced by Lrp2 knockdown in vivo was investigated. Co-injection of BF175 effectively suppressed Lrp2 sh1-induced increases in eye size (FIG. 2).

BF175

Small molecule Fatostatin which is another known inhibitor of SREBP and currently used in clinical trials to treat cancers also increases Lrp2 expression in RPE cells, suggesting its potential to treat high myopia and other eye enlargement disorders.

Fatostatin

Bmp2 is downstream of the Srebp2-Lrp2 pathway and that Bmp2 expression is suppressed by Srebp2 while promoted by Lrp2.

Figure 1A:
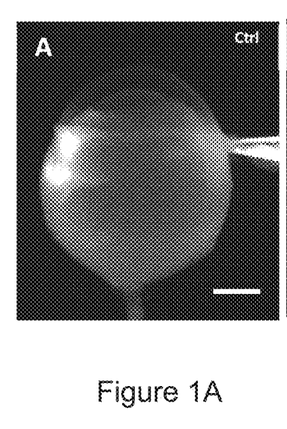
FIG. 1A is an image of a normal mouse eye from a control group.
Figure 1B:
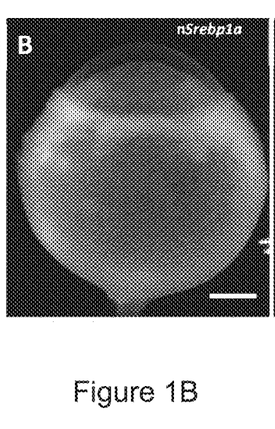
FIG. 1B is an image of an enlarged mouse eye by Srebp1a overexpression.
Figure 1C:
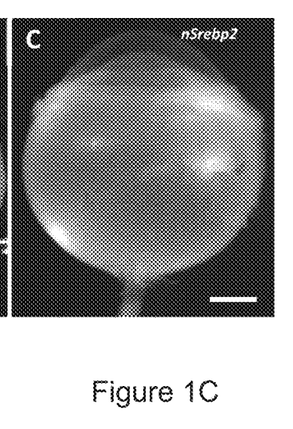
FIG. 1C is an image of an enlarged mouse eye by Srebp2 overexpression.
Figure 1D:
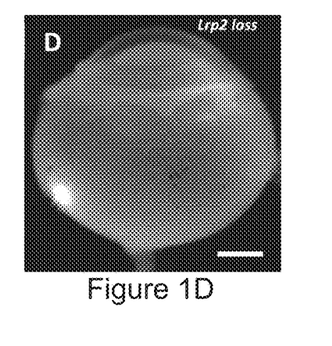
FIG. 1D is an image of an enlarged mouse eye by Lrp2 loss.
Figure 1E:
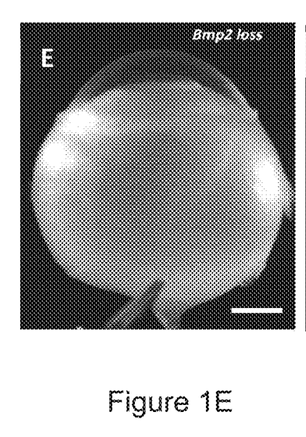
FIG. 1E is an image of an enlarged mouse eye by Bmp2 loss.
Figure 1F:
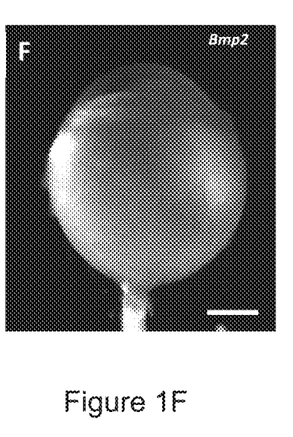
FIG. 1F is an image of a smaller mouse eye by Bmp2 overexpression.
Figure 1G:
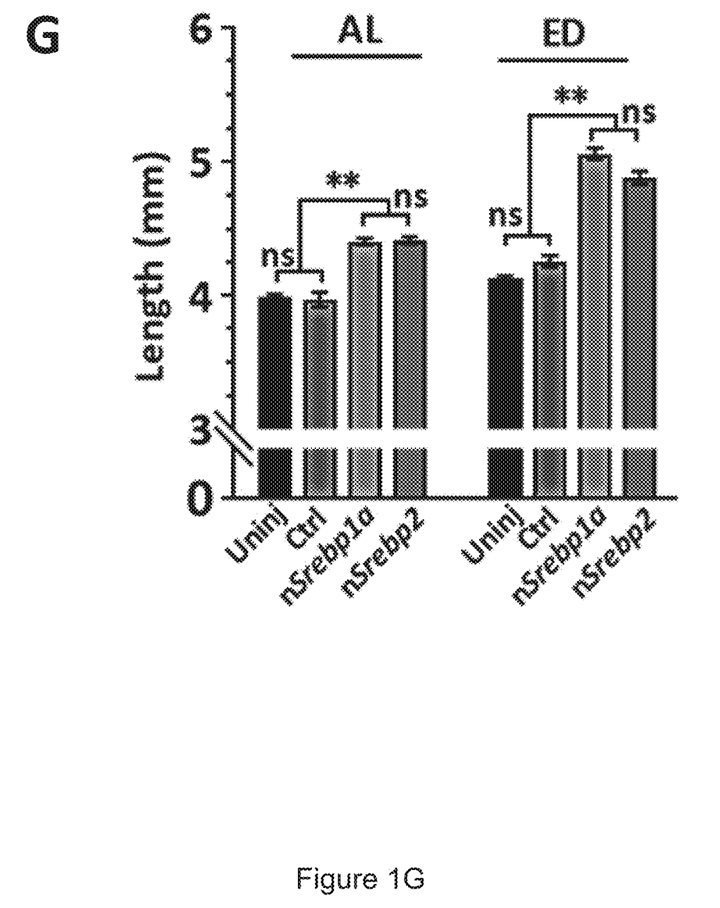
FIG. 1G is a chart showing mouse eye size (Axial length; ED, Equatorial Diameter) regulated by Srebp1a and Srebp2.
Figure 1H:
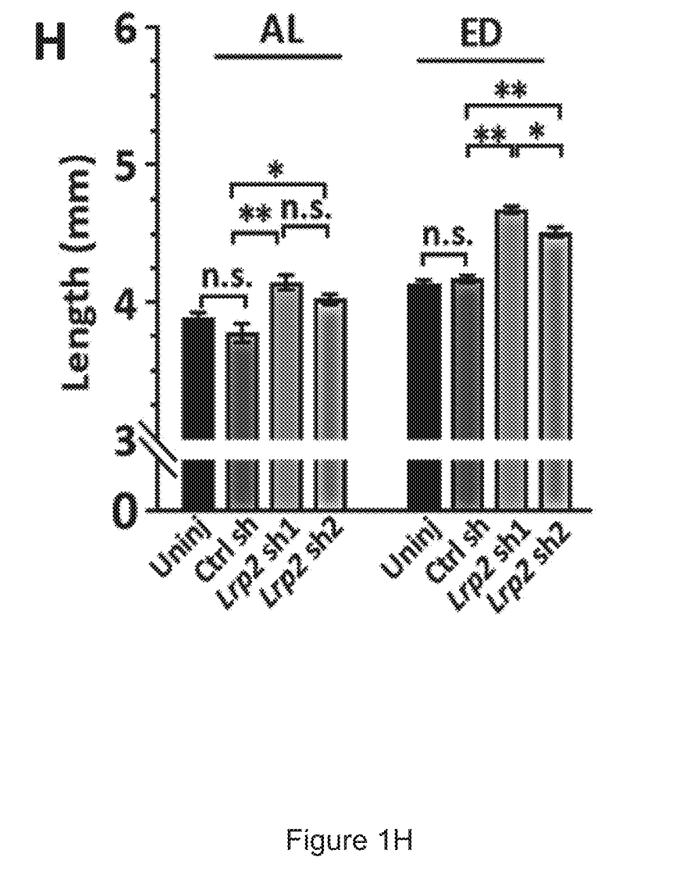
FIG. 1H is a chart showing mouse eye size (Axial length; ED, Equatorial Diameter) regulated by Lrp2 sh1 and Lrp2 sh2.
Figure 1I:
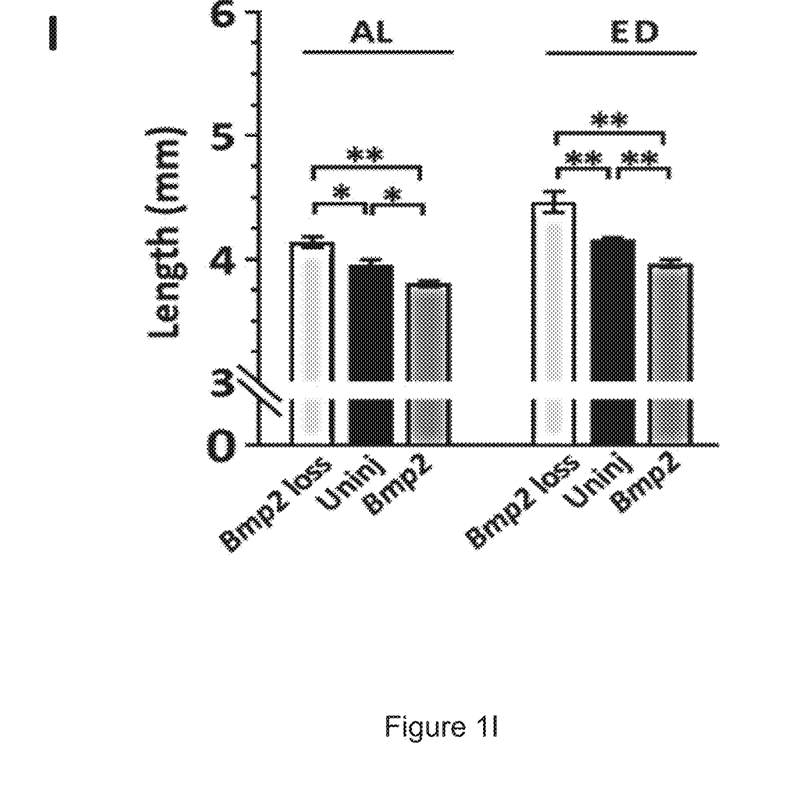
FIG. 1I is a chart showing mouse eye size (Axial length; ED, Equatorial Diameter) regulated by Bmp2.
Figure 2A:
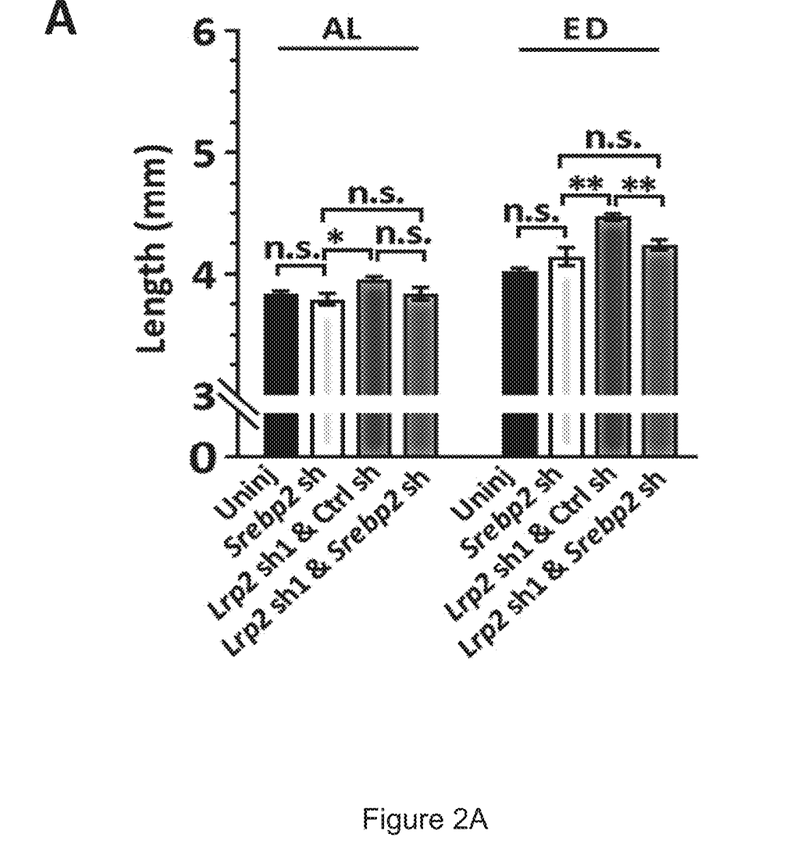
FIG. 2A is a chart showing that enlarged mouse eye size induced by Lrp2 loss can be rescued with Srebp2 shRNA.
Figure 2B:
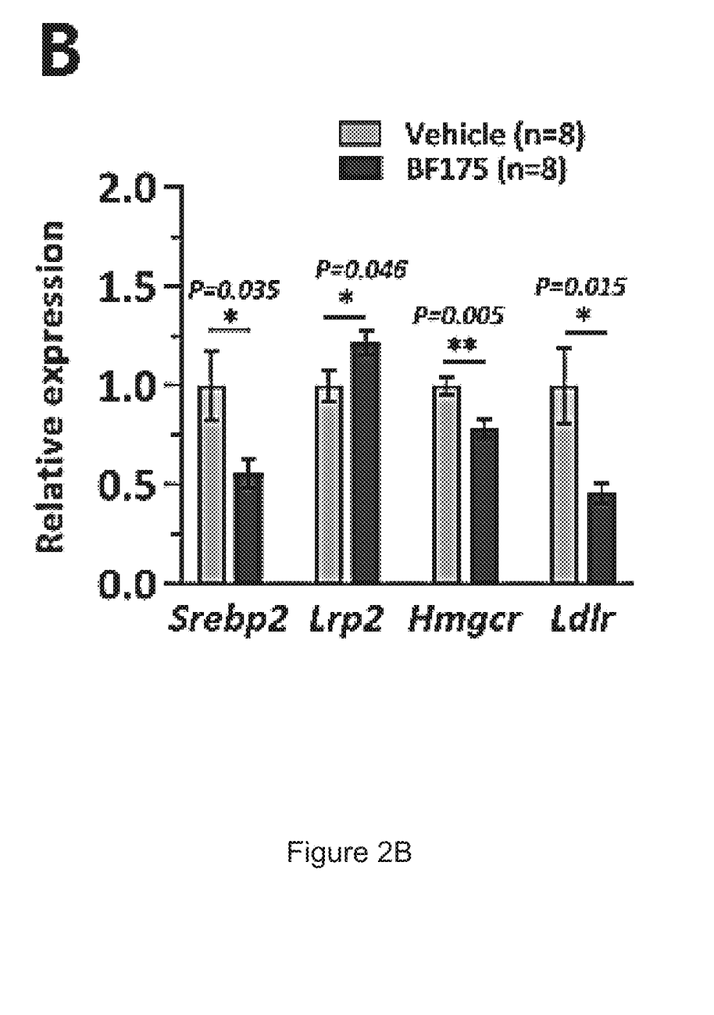
FIG. 2B is a chart showing that Lrp2 gene expression in RPE is increased by SREBP inhibiting drug BF175.
Figure 2C:
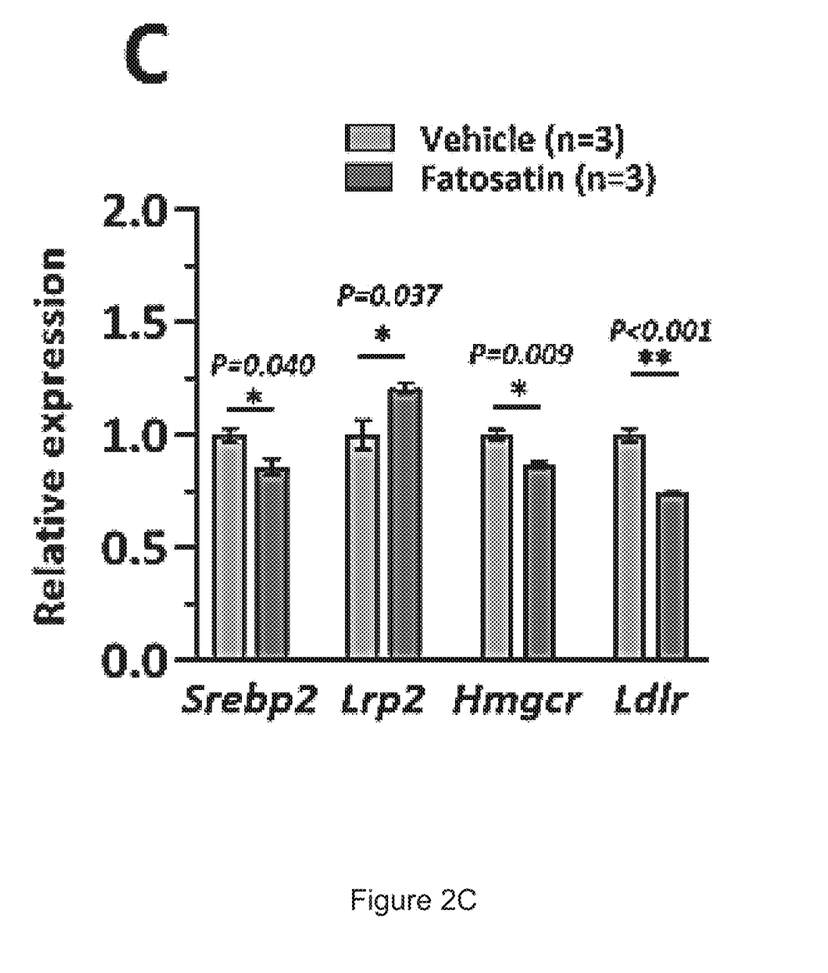
FIG. 2C is a chart showing that Lrp2 gene expression in RPE is increased by SREBP inhibiting drug Fatostatin.
Figure 2D:
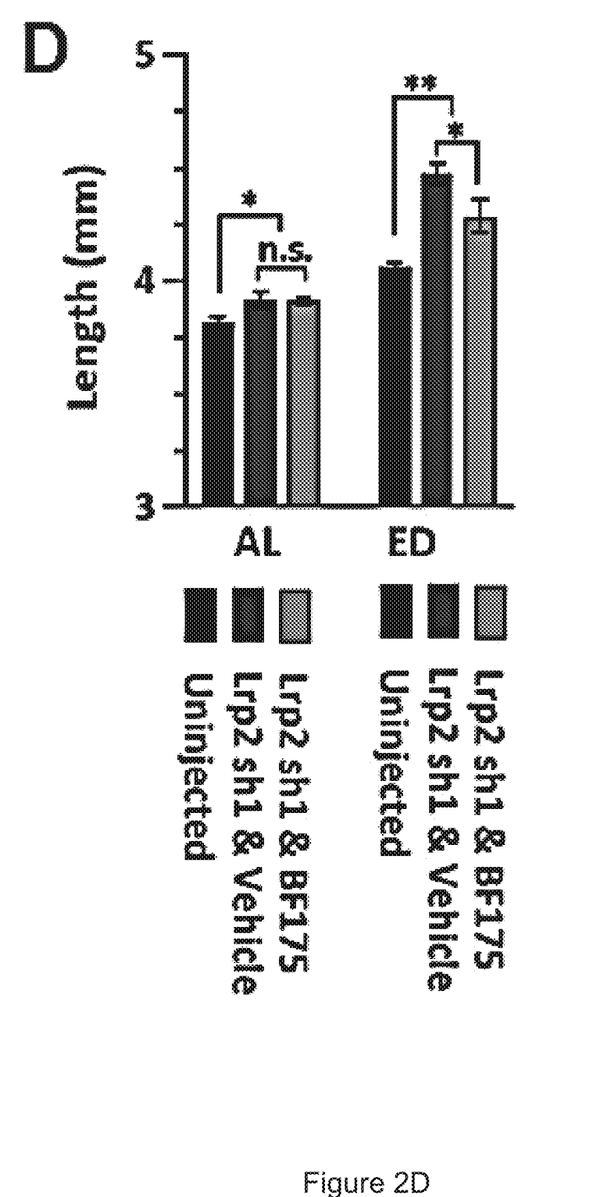
FIG. 2D is a chart showing that enlarged mouse eye size induced by Lrp2 loss can be rescued by SREBP inhibiting drug BF175.
Figure 3A:
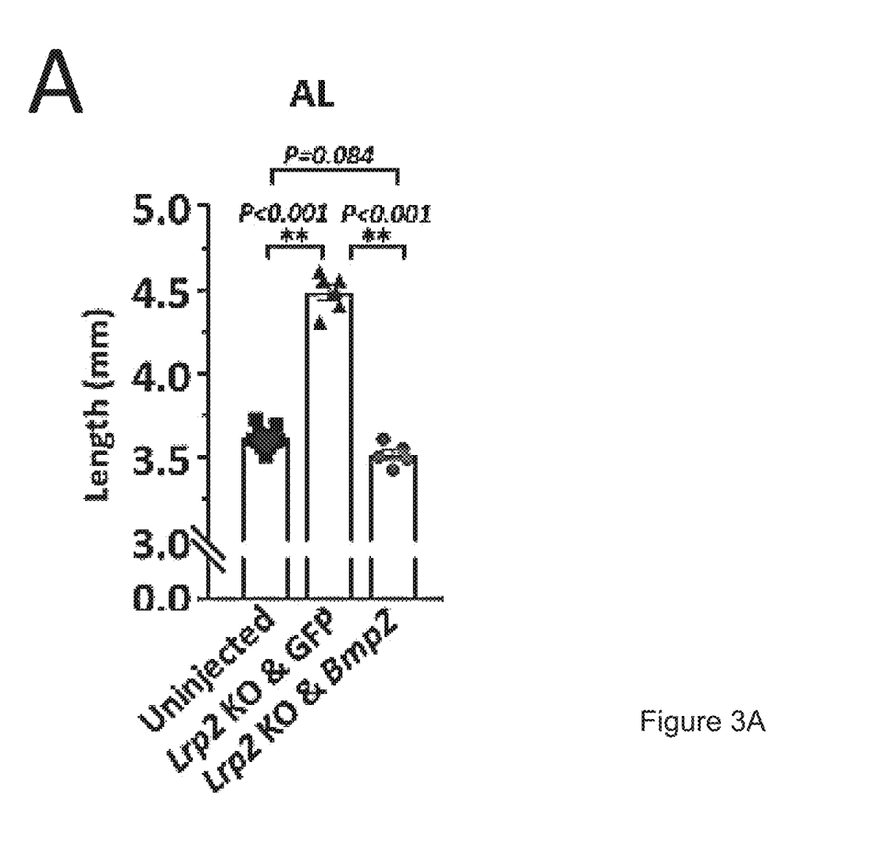
FIG. 3A shows quantification of axial length (AL) in control eyes, Lrp2 knockout (ko) eyes, and Lrp2 ko eyes with Bmp2 overexpression. Bmp2 overexpression can effectively prevent AL increase in Lrp2 ko eyes.
Figure 3B:
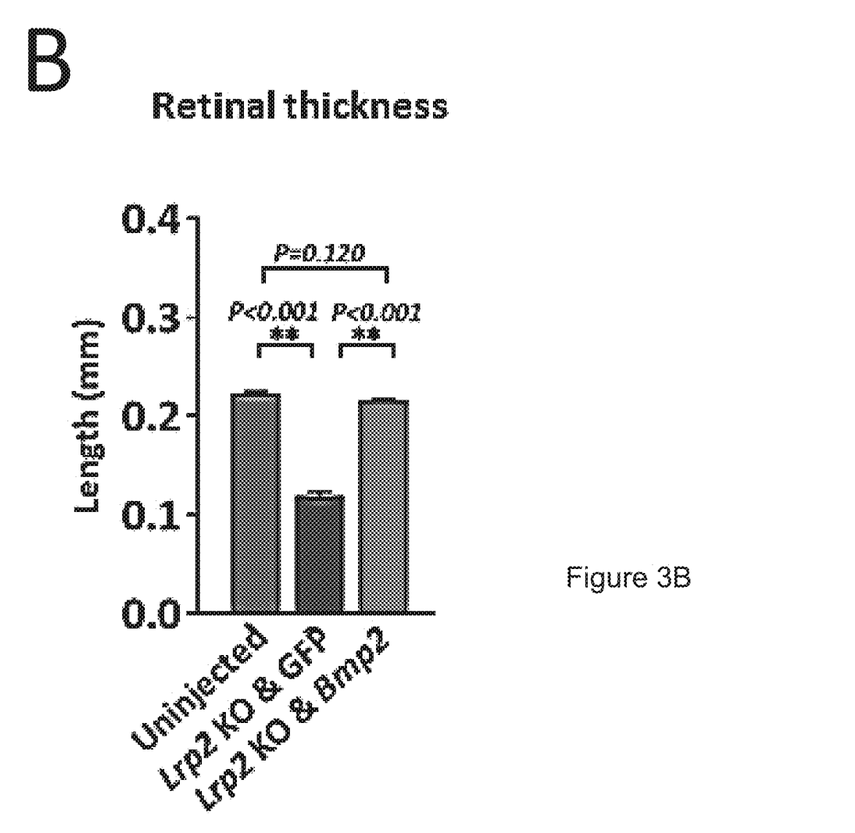
FIG. 3B shows quantification of retinal thickness in control eyes, Lrp2 knockout (ko) eyes, and Lrp2 ko eyes with Bmp2 overexpression. Bmp2 overexpression can effectively prevent retinal thinning in Lrp2 ko eyes.
Figure 3C:
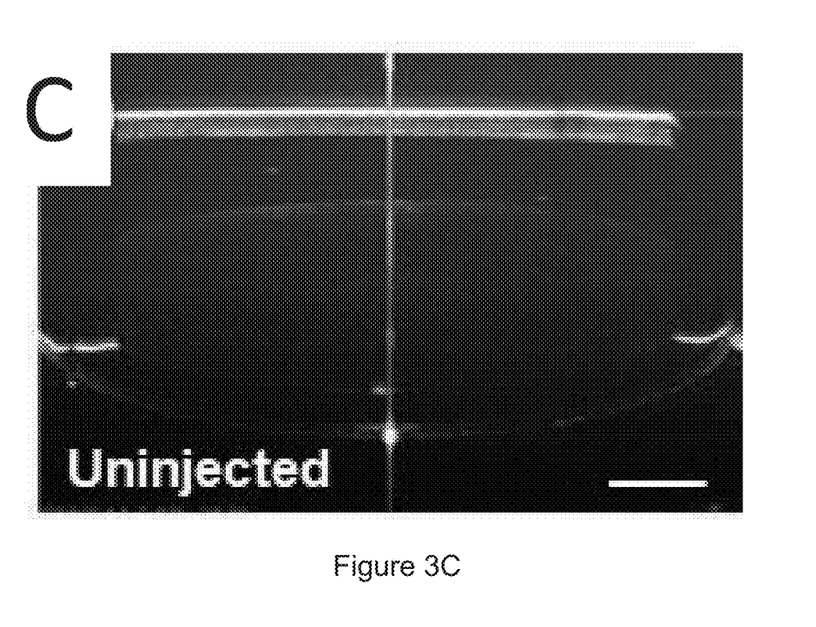
FIG. 3C shows biometry measurement with optical coherence tomography for an uninjected eye.
Figure 3D:
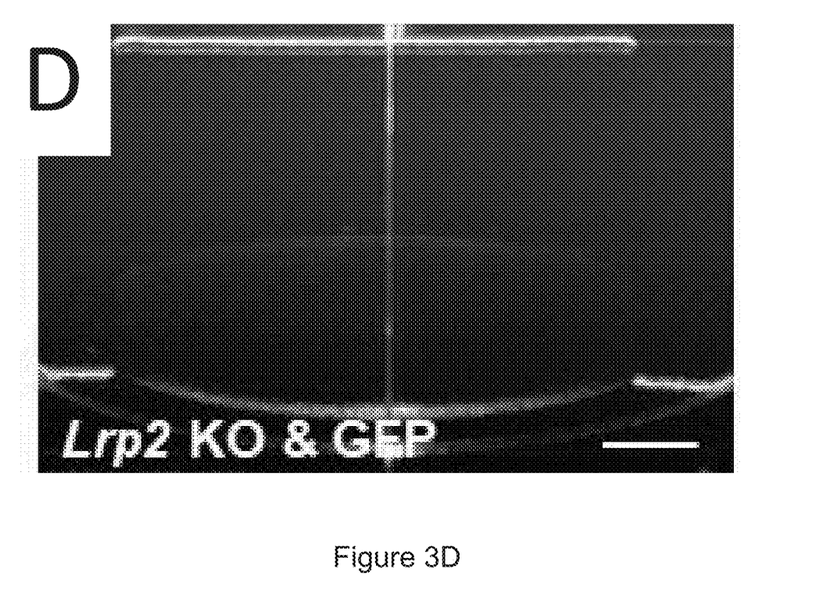
FIG. 3D shows biometry measurement with optical coherence tomography for an eye injected with Lrp2 KO & GFP. Note the increase of axial length and vitreous chamber depth.
Figure 3E:
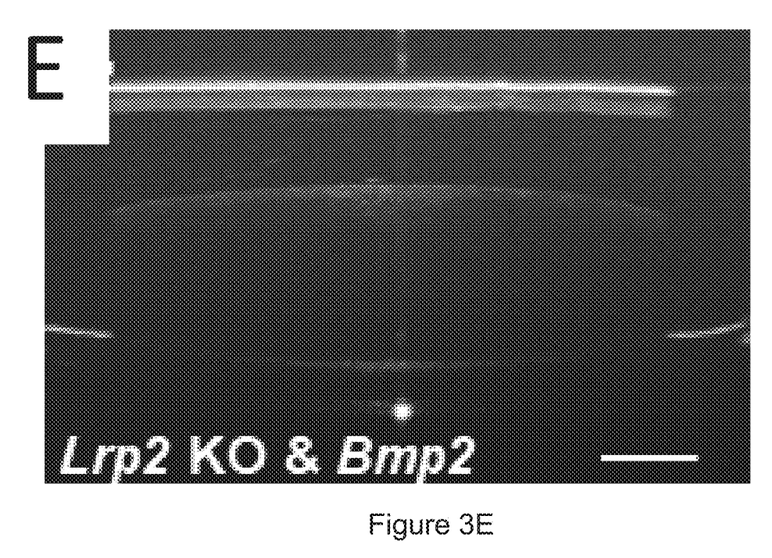
FIG. 3E shows biometry measurement with optical coherence tomography for an eye injected with Lrp2 KO & Bmp2. Note the normal axial length and vitreous chamber depth.
Figure 3F:
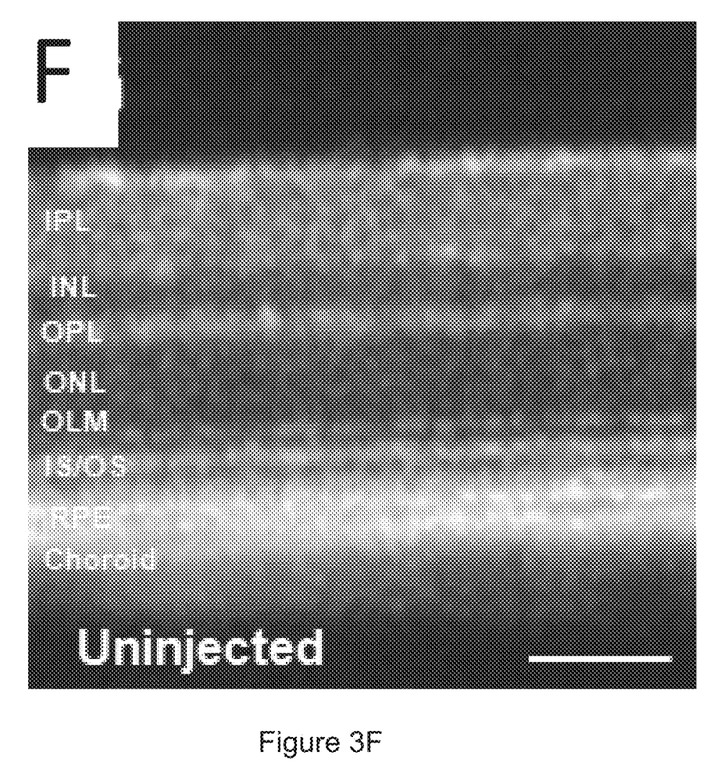
FIG. 3F shows normal retinal layers of an uninjected control eye by optical coherence tomography.
Figure 3G:
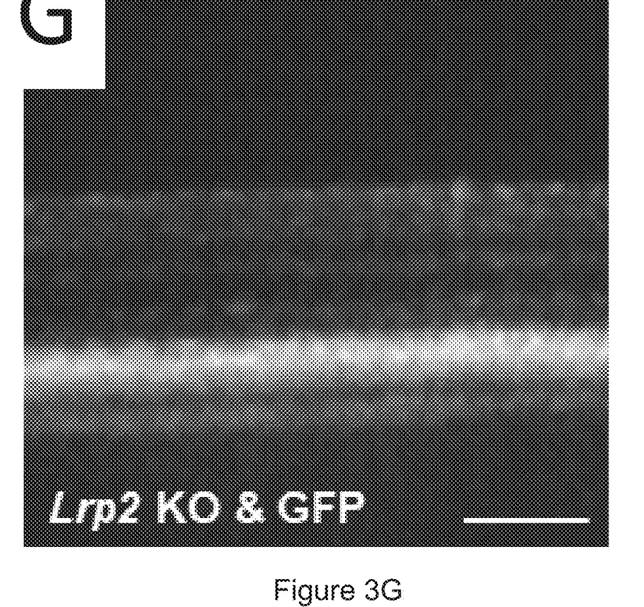
FIG. 3G shows thinner retina of a Lrp2 KO eye injected with GFP control virus by optical coherence tomography
Figure 3H:
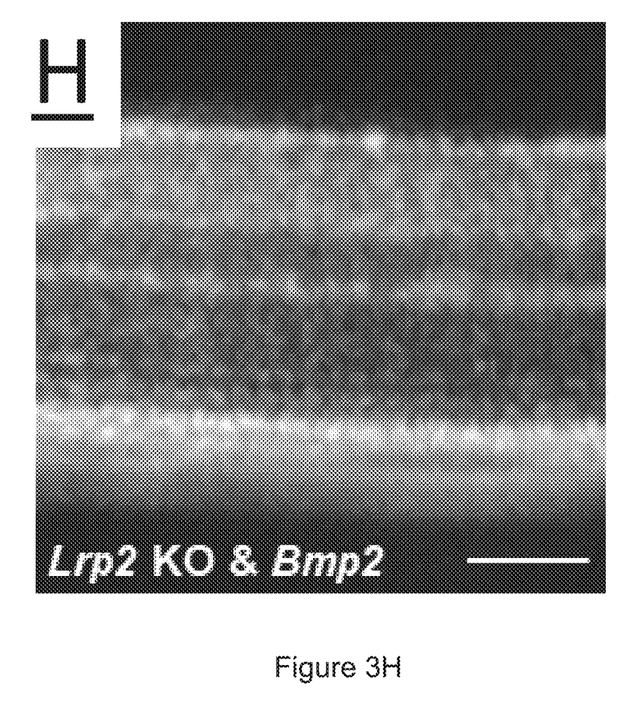
FIG. 3H shows normal retinal thickness of a Lrp2 KO eye injected with Bmp2 virus by optical coherence tomography.

To find out whether BMP2 is the key BMP ligand that controls postnatal eye size, Bmp2 in mouse RPE was knocked down. Bmp4, Bmp6, Bmp7 or Bmp11 was also knocked down one by one for comparison, and two shRNAs with high knockdown efficiency for each gene were tested. It was found that injection of AAV-Best1-Bmp2 sh1 or sh2 induced the most significant eye enlargement phenotype. Downregulation of Bmp4, 6, 7 and 11 did not cause any significant change in eye size. Bmp2 was the key effector downstream of Srebp2 and Lrp2 in regulating eye size and that Bmp2 downregulation was the cause of eye enlargement. The loss-of-function assay suggested that BMP2 is a STOP signal of eye growth. Too much BMP2 prevented the eye globe from reaching a normal size; Bmp2 overexpression in the RPE led to microphthalmos, with significant decreases in both AL and ED (FIG. 1).

In humans, mutations in the LRP2 gene leads to DB/FOAR syndrome, which is currently untreatable. LRP2 is a large transmembrane protein with a molecular weight close to 600 kDa. Known LRP2 mutations are likely loss-of-function mutations, affecting protein trafficking or stability. Given its large size, it is difficult to rescue Lrp2 loss-of-function phenotypes by gene augmentation therapy. Given the data that Bmp2 is downstream of Lrp2 and that Bmp2 functions to restrict eye growth, it was hypothesized that increasing Bmp2 expression level could rescue the ocular phenotypes caused by Lrp2 loss. To test this hypothesis, Lrp2 conditional knockout mice (Lrp2 cko) was induced by injecting AAV8-Best1-Cre virus into Lrp2 fl/fl mice. AAV8-Best1-Bmp2 was co-injected for treatment and eye size was measured by optical coherence tomography (OCT). Axial length increase in Lrp2 cko mice was completely rescued by AAV8-Best1-Bmp2 (FIG. 3).

In highly myopic eyes caused by Lrp2 knockdown, the retinas were thinner due to the expansion of the posterior eye segment and the flattening of retina tissue. Retinal thinning was also rescued by Bmp2 overexpression (FIG. 3). These results suggest that targeted Bmp2 expression in the RPE is an effective therapeutic intervention for excessive ocular growth caused by Lrp2 loss.

Materials and Methods

AAV Production pAAV, Rep/Cap 2/8, and adenoviral helper plasmids were mixed with polyethylenimine and added to HEK293T cells. 24 hr after transfection, cell medium was changed to DMEM only. 72 hr after transfection, supernatant was collected and cell debris was spun down and discarded. AAV8 in the supernatant were precipitated by PEG-8000 (8.5% wt/vol PEG-8000 and 0.4M NaCl for 1.5 hr at 4 degree), centrifuged at 7000×g for 10 min, and resuspended in virus buffer (150 mM NaCl and 20 mM Tris, pH 8.0). The resuspend was run on an iodixanol gradient, and viruses in 40% fraction were collected. Recovered AAV virus particles were washed three times with cold PBS using Amicon 100K columns (EMD Millipore). Protein gels were run to determine virus titers.

Subretinal Injection of AAV or BF175

Subretinal injection into P0 (P2 for AAV-RK-viruses) neonate eyes was performed as known in the art. Approximately 0.25 μl of viruses in PBS was injected into the subretinal space using a pulled angled glass pipette controlled by a FemtoJet (Eppendorf). BF175 stock solution (25 mM in DMSO) was first mixed with Tween-20 (Sigma-Aldrich) at a ratio of 5:1 in order to help BF175 dissolve in PBS. Then the mixed solution was added to the virus to a final BF175 concentration of 12.5 uM. The vehicle treatment was virus added with the same amount of DMSO with Tween-20. For animals used for qPCR and RNA-seq, both left and right eyes were injected and used for RNA extraction. For animals used for eye size measurement or other phenotype characterizations, only the right eye of the animal was injected, and the fellow left eye was uninjected for with-in animal controls.

Eye Globe Dimension Measurement

CD-1 mice were sacrificed at indicated ages. Eyes were enucleated, and connective tissues and muscles were carefully removed using tweezers and scissors. Eyes were immersed in PBS in 6 cm petri dish and imaged under a Nikon SMZ800N dissection scope with 2× magnification. ED and AL were measured in imageJ and converted to millimeters.

OCT

OCT images of mouse eyes were taken using a SD-OCT (Bioptigen Envisu R4310 SD-OCT, Germany). Detailed procedures can be found in Supplementary Information.

RPE Explant

Eyes were quickly removed from the euthanized mouse and dipped in 70% ethanol for decontamination. Under a dissecting stereomicroscope, connective tissues and muscles were carefully removed. After washing twice in PBS, eyes were immersed in warm culture medium (DMEM:F12+10% FBS). Cornea was cutoff using curved scissors, and lens was pulled out gently with tweezers. Or a serrate was cut off to remove iris and cornea. Retina and optic nerve were carefully and completely removed from eye cups. Four radial cuts were made to enable flat-mounting of eye cups. Each eye cup was transferred onto the center of a floating polycarbonate nucleopore filter membrane (Whatman 110406, 0.2 Micron) placed in 6-well plates with the RPE side facing down. The freshly prepared BF175 stock solution was added to the full culture medium to a final BF175 concentration of 12.5 uM. Half of the medium was replaced with fresh medium on the second day. RPE flat-mounts were harvested at 48 hr in explant and processed for RPE isolation and RNA extraction.

Mouse RPE Cells Isolation

Eyecups without retina and optic nerve tissues were dissected as described in the RPE explant section. Two eyes of the same mouse were pooled in one tube and processed together. RPE were incubated in papain solution (Worthington) for 15 minutes. After washing twice in warm medium, RPE were triturated with 600 μl pipette tip gently to disso- ciate the pigmented RPE cells from sclera. Resuspended cell solution was transferred to a clean tube and spun down at 600 g.

qPCR

RNAs were converted to cDNA using PrimeScript RT reagent kit with gDNA Eraser (Takara). qPCR was performed using PowerUp Sybr Green Master Mix (Thermofisher) on QuantStudio 3 Real-Time PCR stems (Applied Biosystems). Gapdh was used as the normalizing control. qPCR primers were listed in Supplementary Information.

BF175 Synthesis:

Preparation of compound 2 A solution of 4-iodotoluene (465 mg, 2.13 mmol) in DMSO (10 mL) was added into a mixture of 1,1'-bis(diphenyl phosphino)ferrocene]dichloropalladium(II) [PdCl2(dppf)] (78 mg, 0.11 mmol), potassium acetate (KOAc, 0.60 g, 6.11 mmol) and bis(pinacolato) diboron (0.60 g, 2.36 mmol) in a Schlenk flask under nitrogen. The mixture was stirred at 80° C. overnight. The crude product was extracted with ethyl acetate (EtOAc), washed with water, and then dried with MgSO4. The solvent was evaporated under reduced pressure. The product was purified by silica gel column chromatography (EtOAc/hexane 1:50) to afford compound 2 (369 mg, 79%) as a white solid. 1H NMR (400 MHz, CDCl3): 7.73 (d, J=7.2 Hz, 2H), 7.21 (d, J=7.2 Hz, 4H), 2.39 (s, 3H), 1.37 (s, 12H).

Preparation of compound BF175: A mixture of compound 3 (560 mg, 1.0 mmol) and sodium tert-butoxide (tBuONa, 288 mg, 3.0 mmol) in DMF (10 mL) was stirred at room temperature under nitrogen for 10 min. To this solution, 3,5-dichlorobenzaldehyde (175 mg, 1.0 mmol) was added and the resulting mixture was stirred at room temperature for 6 h. The reaction mixture was treated with water (20 mL) and neutralized with 1 M HCl, then extracted with EtOAc (3×10 mL), washed with brine, and finally dried with MgSO4. The solvent was evaporated under reduced pressure. The product was purified by silica gel column chromatography (EtOAc/hexane 1:10) to afford a mixture of E/Z BF175 (161 mg, 43%) as a white solid. 1H NMR (400 MHz, CDCl3): 7.82 (d, J=8.0 Hz, 2H), 7.49 (d, J=8.0 Hz, 2H), 7.37 (d, J=2.0 Hz, 2H), 7.24 (t, J=1.6 Hz, 1H), 7.11 (d, J=16.4 Hz, 1H), 7.01 (d, J=16.4 Hz, 1H), 1.36 (s, 12H).

SEQUENCE LISTING

```
<160> NUMBER OF SEQ ID NOS: 2

<210> SEQ ID NO 1
<211> LENGTH: 59
<212> TYPE: DNA
<213> ORGANISM: Artificial Sequence
<220> FEATURE:
<223> OTHER INFORMATION: SYNTHETIC

<400> SEQUENCE: 1
tcttgtcatt gatagaagac cgttttggcc actgactgac ggtcttctca atgacaaga      59

<210> SEQ ID NO 2
<211> LENGTH: 59
<212> TYPE: DNA
<213> ORGANISM: Artificial Sequence
<220> FEATURE:
<223> OTHER INFORMATION: SYNTHETIC

<400> SEQUENCE: 2
tgattgctga caaactgtag cgttttggcc actgactgac gctacagtgt cagcaatca      59
```

Preparation of compound 3: A mixture of compound 2 (1.53 g, 7.02 mmol), N-bromosuccinimide (NBS, 1.87 g, 10.5 mmol), and azobisisobutyronitrile (AIBN, 12 mg, 73 mol) in acetonitrile (MeCN, 100 mL) was refluxed at 90° C. for 2 h. After the reaction was completed, the mixture was allowed to cool at room temperature and the solvent was removed by rotary evaporation. Hexane was added to dissolve the product and the remaining solid was removed by filtration. The filtrate was concentrated and dried in vacuo to afford the brominated product. The brominated product and triphenylphosphine (PPh3, 1.68 g, 6.41 mmol) in MeCN (20 mL) was heated at 90° C. After 12 h, the reaction mixture was cooled to room temperature, and the solvent was removed under vacuum. The crude product was then washed with diethyl ether (3×5 mL) to give the desired compound 3 (2.82 g, 72%) as a white solid. 1H NMR (400 MHz, CDCl3): 7.77-7.67 (m, 9H), 7.64-7.59 (m, 6H), 7.53 (d, J=7.6 Hz, 2H), 7.03 (dd, J=2.4, 8.4 Hz, 2H), 5.35 (d, J=14.8 Hz, 2H), 1.30 (s, 12H).

What is claimed is:

1. A method of treating Donnai-Barrow syndrome in a subject in need thereof, comprising a step of administering to the subject a recombinant adeno-associated virus (AAV) vector comprising a nucleic acid encoding a normal bone morphogenetic protein 2 (BMP2) gene operably linked to a human Bestrophin1 (hBEST1) promoter and a Simian virus 40 (SV40) intron, wherein the AAV vector is administered by subretinal injection and can increase the expression of BMP2 in the subject, and rescue eye enlargement phenotype.

2. The method of claim 1, wherein AAV vector is administered by subretinal injection to contact Retinal Pigment Epithelium (RPE) cells of the subject.

3. The method of claim 1, wherein the AAV vector further comprises a woodchuck hepatitis virus post-transcriptional regulatory element (WPRE) and a bovine growth hormone polyadenylation (BGH-PolyA) sequence.

* * * * *